(12) United States Patent
Sutton et al.

(10) Patent No.: US 10,088,157 B2
(45) Date of Patent: Oct. 2, 2018

(54) MULTI-SENSOR PROBE FOR MONITORING COMBUSTION IN A CONDUIT

(71) Applicant: ALSTOM Technology Ltd, Baden (CH)

(72) Inventors: James P. Sutton, South Windsor, CT (US); Rebecca Lynn Tobiasz, Suffield, CT (US); David J. Matteson, Knoxville, TN (US); Allan Gunn Ferry, Windsor, CT (US); Robert Federick Murphy, Wethersfield, CT (US); Christopher Daniel Curl, Branford, CT (US)

(73) Assignee: GENERAL ELECTRIC TECHNOLOGY GMBH, Baden (CH)

( * ) Notice: Subject to any disclaimer, the term of this patent is extended or adjusted under 35 U.S.C. 154(b) by 733 days.

(21) Appl. No.: 14/630,473

(22) Filed: Feb. 24, 2015

(65) Prior Publication Data

US 2016/0245516 A1    Aug. 25, 2016

(51) Int. Cl.
*F23N 3/00* (2006.01)
*F23N 5/24* (2006.01)
(Continued)

(52) U.S. Cl.
CPC .............. *F23N 3/002* (2013.01); *F23N 5/006* (2013.01); *F23N 5/242* (2013.01); *G01N 1/2258* (2013.01);
(Continued)

(58) Field of Classification Search
CPC .......... F23N 3/002; F23N 5/006; F23N 5/242; F23N 2025/04; F23N 2025/08;
(Continued)

(56) References Cited

U.S. PATENT DOCUMENTS

| 4,578,986 A | 4/1986 | Navarre |
| 4,852,384 A | 8/1989 | Woolbert et al. |

(Continued)

FOREIGN PATENT DOCUMENTS

| CN | 102008930 A | 4/2011 |
| CN | 102445090 A | 5/2012 |

(Continued)

OTHER PUBLICATIONS

Translation JP 07269851 A.*

(Continued)

*Primary Examiner* — Natalie Huls
*Assistant Examiner* — Monica S Young
(74) *Attorney, Agent, or Firm* — GE Global Patent Operation; Stephen G. Midgley

(57) ABSTRACT

A gas outlet monitoring system for a boiler system includes a gas probe(s) with a plurality of gas sensing locations wherein each location measures a plurality of parameters of the gas flow, such a oxygen concentration and temperature. The multi-sensor probe includes a tubular lance and a plurality of sensor pods spaced along the lance. Each sensor pod has an oxygen sensor disposed in a first port, and a first temperature sensor disposed in a second port. An enclosure is disposed at one end of the tubular lance. The enclosure has a respective pressure sensor for each oxygen sensor port. A plurality of first tubes passes through the lance between the enclosure and the first port of a respective sensor pod to provide a gas to the respective first port for the purpose of providing cleaning air. A plurality of second tubes passes through the lance between the enclosure and the first port of a respective sensor pod to provide fluid communication between gas in the respective first port and the respective pressure sensor. One pressure sensor is provided for each oxygen sensor.

17 Claims, 10 Drawing Sheets

(51) Int. Cl.
*F23N 5/00* (2006.01)
*G01N 1/22* (2006.01)

(52) U.S. Cl.
CPC ...... *F23N 2025/04* (2013.01); *F23N 2025/08* (2013.01); *F23N 2900/05001* (2013.01); *F23N 2900/05002* (2013.01); *F23N 2900/05003* (2013.01); *F23N 2900/05006* (2013.01)

(58) Field of Classification Search
CPC . F23N 2900/05001; F23N 2900/05002; F23N 2900/05003; F23N 2900/05006; G01N 1/2258
USPC .......................................................... 73/232
See application file for complete search history.

(56) References Cited

U.S. PATENT DOCUMENTS

| | | | |
|---|---|---|---|
| 6,381,504 | B1 | 4/2002 | Havener et al. |
| 6,712,604 | B2 | 3/2004 | Havlena |
| 7,966,080 | B2 | 6/2011 | Jia et al. |
| 8,626,450 | B2 | 1/2014 | Dooley |
| 2004/0149579 | A1* | 8/2004 | Palmer ............... G01N 27/4074 204/431 |
| 2007/0137318 | A1* | 6/2007 | Desrochers ............. G01N 1/26 73/863.81 |
| 2009/0223466 | A1 | 9/2009 | Knorr, Jr. |
| 2010/0037678 | A1* | 2/2010 | Chothani ............... G01N 27/14 73/25.01 |
| 2014/0290329 | A1* | 10/2014 | Kramer .................. F23N 5/006 73/1.57 |
| 2014/0360249 | A1 | 12/2014 | Ferry |

FOREIGN PATENT DOCUMENTS

| | | |
|---|---|---|
| CN | 103528387 A | 1/2014 |
| JP | 07269851 A * | 10/1995 |

OTHER PUBLICATIONS

Use of Artificial Neural Networks Process Analyzers: A Case Study, Al-Duwaish et al, ISBN 2-930397092091, pp. 465-470, Apr. 24-26, 2002.
Flue Gas Oxygen Analyzers—GE Sensing, 2008.
Flue Gas Analysis as a Diagnostic Tool for Fired Process Heater Furnaces, Rosemount Analytical—Emerson Process Management, 2013.
Oxymitter™ 4000 in Situ Oxygen Transmitter—Rosemount Analytical—Emerson Process Management, Oct. 9, 2014.
copy of PCT Search Report and Written Opinion issued in connection with corresponding PCT Application No. PCT/ S2016/017692 on May 19, 2016.

* cited by examiner

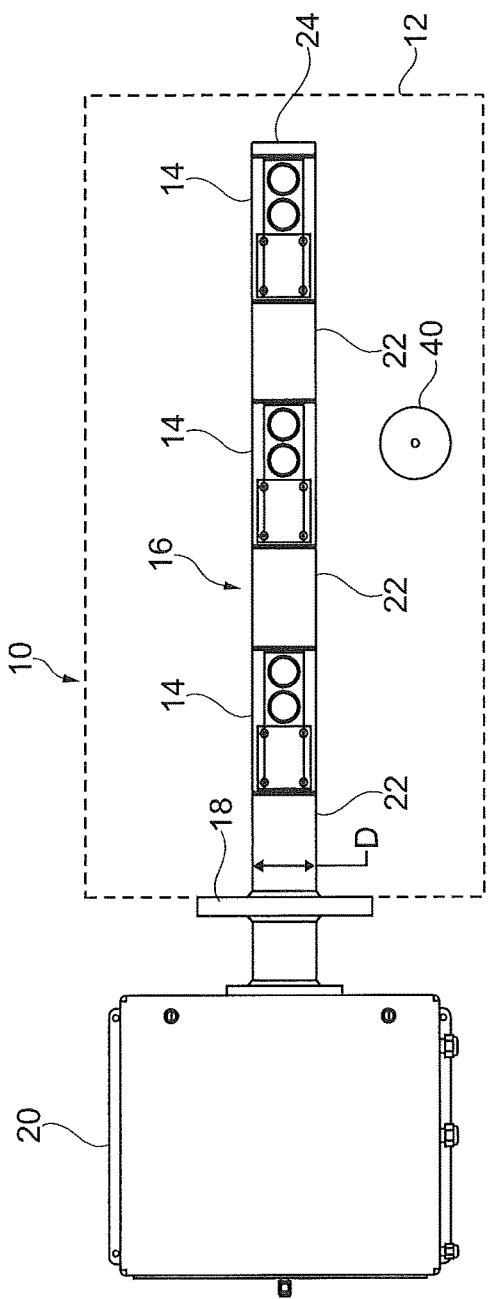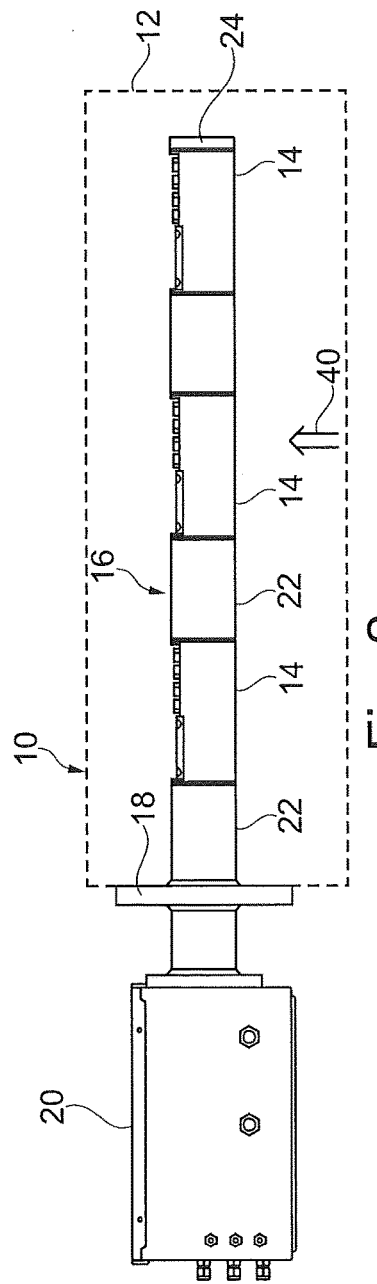

MULTI-SENSOR PROBE FOR MONITORING COMBUSTION IN A CONDUIT

TECHNICAL FIELD

The present disclosure relates generally to a system for monitoring the gas flowing through a duct and more specifically, to a gas outlet monitoring system for a boiler system having a gas probe(s) with a plurality of gas sensing locations wherein each location measures a plurality of parameters of the gas flow.

BACKGROUND

Long recognized as crucial elements of controlling a boiler are fuel/air mixing, fuel/air ratio and achieving ignition energy for combustion. Optimal combustion is stable, has high energy conversion of the fossil fuel to $CO_2$, minimum NOx and CO in the flue gas, and minimum harmful intermediaries (such as Hydrogen Sulfides) on the combustion walls. The financial benefits of low excess air operation are significant and include increased efficiency and cost savings in air pollution control equipment. Historically, boilers were designed to combust at 18 to 20% excess air to insure full combustion of the fossil fuel occurred. However, it has been demonstrated that operating at lower amount of excess air, for example 12%, can achieve a significant cost savings. The fundamental limitation in operating with low excess air is incomplete combustion resulting in increased CO along with hazardous air pollutant (HAP) emissions. Consequently, it is critical to have a gas monitoring system capable of continuously and accurately measuring the composition of the flue gas exiting the boiler, such as the oxygen.

Unfortunately, current oxygen monitoring systems are insufficient to operate a boiler at lower excess oxygen levels in the flue gas because the oxygen sensors and methods for measuring the oxygen within the flue gas do not provide a complete and reliable measurement of the oxygen level and have a tendency to drift which may cause the boiler to deviate from optimal operation.

Currently, existing commercial oxygen probes measure the oxygen concentration at only one, or only a few locations. Optimizing boiler combustion requires a good understanding of the oxygen concentration and gas temperature across a large gas duct (up to 30 feet wide). To achieve a good understanding of the oxygen concentration and temperature within a duct, including imbalances across the duct, experience has shown that a minimum of 12 to 16 measurement location is required. Installing 12 or more individual zirconium oxide sensors to measure O2 concentrations, plus an equal number thermocouples to measure temperature involves many separate pieces of equipment/sensors which must be mounted, connected, powered, and maintained. The total installation cost of such a system is large, and prevents many boilers from being fully instrumented with traditional sensors.

Similarly, extractive gas measurement systems are widely used for boiler performance and emissions testing. However, these systems are generally not suited for long-term continuous operation for several reasons. Many of the chemical analyzers typically used may not support long term continuous operation, or require very frequent maintenance. Filters on the gas extraction grid clog, and require periodic cleaning. Gas cooling and drying equipment is required before the extracted boiler gas can be fed to many chemical analyzers, and this equipment requires frequent maintenance. Many of the extractive systems sample from a single location at a time, and cannot provide multiple simultaneous measurements at each sample location.

SUMMARY

According to the aspects illustrated herein, there is provided a multi-sensor probe comprising a tubular lance, and a plurality of sensor pods spaced along the lance. Each sensor pod includes an oxygen sensor disposed in a first port, and a first temperature sensor disposed in a second port. An enclosure is disposed at one end of the tubular lance, wherein the enclosure has a respective pressure sensor. A plurality of first tubes passes through the lance between the enclosure and the first port of a respective sensor pod to provide a gas to the respective first port A plurality of second tubes passes through the lance between the enclosure and the first port of a respective sensor pod to provide fluid communication between gas in the respective first port and the respective pressure sensor.

According to the other aspects illustrated herein, a method for measuring constituents of a gas flowing a conduit includes measuring the oxygen concentration and the temperature within the conduit at multiple locations within the duct using at least one multi-sensor probe extended within the duct. The multi-sensor probe includes a tubular lance a plurality of sensor pods spaced along the lance. Each sensor pod has an oxygen sensor disposed in a first port, a first temperature sensor disposed in a second port, an enclosure disposed at one end of the tubular lance. The enclosure has a respective pressure sensor. The multi-sensor probe further includes a plurality of first tubes passing through the lance between the enclosure and the first port of a respective sensor pod to provide a gas to the respective first port. A plurality of second tubes passes through the lance between the enclosure and the first port of a respective sensor pod to provide fluid communication between gas in the respective first port and the respective pressure sensor. An operational parameter of the boiler is controlled in response to the plurality of temperature and oxygen measurements provided from the multi-sensor probe.

According to the other aspects illustrated herein, gas outlet monitoring system for controlling the operation of a boiler includes a plurality of multi-sensor probes disposed within a duct of the boiler. Each multi-sensor probe includes a tubular lance and a plurality of sensor pods spaced along the lance. Each sensor pod has an oxygen sensor disposed in a first port and a first temperature sensor disposed in a second port. An enclosure is disposed at one end of the tubular lance, wherein the enclosure has a respective pressure sensor. A plurality of first tubes passes through the lance between the enclosure and the first port of a respective sensor pod to provide a gas to the respective first port. A plurality of second tubes passes through the lance between the enclosure and the first port of a respective sensor pod to provide fluid communication between gas in the respective first port and the respective pressure sensor. A processor controls an actuator to change an operation parameter of the boiler in response to the respective oxygen concentration and temperature provided by the sensor pods of the respective multi-sensor probes.

The above described and other features are exemplified by the following figures and detailed description.

BRIEF DESCRIPTION OF THE DRAWINGS

Referring now to the figures, and wherein the like elements are numbered alike:

FIG. 1 is a front plan view of a gas sensor of gas outlet monitoring system according the present invention.

FIG. 2 is a side plan view of the gas sensor of FIG. 1.

DETAILED DESCRIPTION

Figure 3:
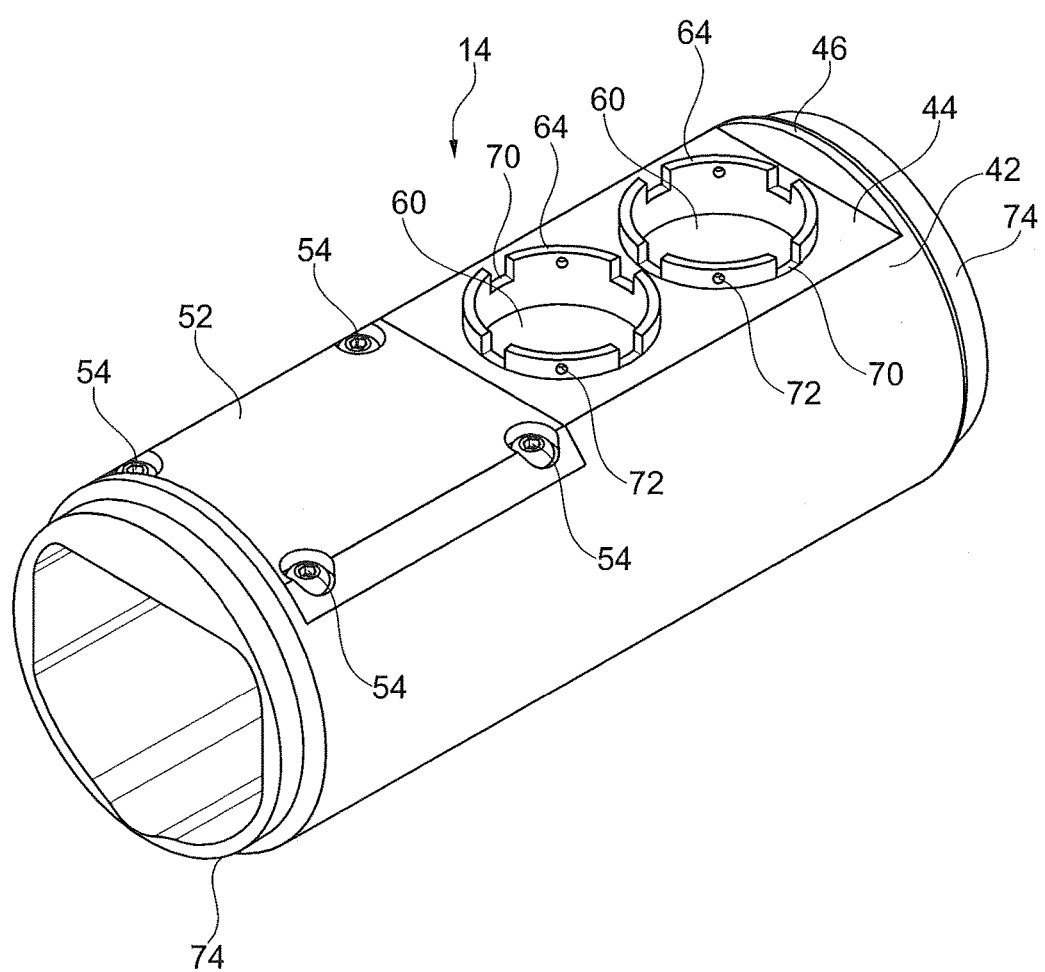
FIG. 3 is a perspective view of a sensor pod of the gas sensor of FIG. 1.

Disclosed herein is a multi-sensor probe 10 use to measure and monitor the constituents of a gas flowing through a gas duct or gas outlet 12. The multi-sensor probe 10 provides a plurality of sensor pods 14 dispose at spaced location along a lance portion 16 of the multi-sensor probe. One or more multi-sensor probes 10 may be inserted within a duct 12 to measure a plurality of parameters of the gas flowing therethrough as well as providing a location or profile of the measurements across the cross-sectional area of the duct. These multiple measurements across the cross-sectional areal of the duct 12 may be used to control associated equipment, e.g. a boiler plant, or monitor the operation of associated equipment, e.g., an air heater.

Referring to FIGS. 1 and 2, a multi-sensor probe 10 includes a lance 16 having a plurality of sensor pods 14 spaced at a pre-determined distance along its length. The lance 16 includes a collar 18 for securing the probe 10 to the duct or conduit 12 having gas passing therethrough. The collar 18 includes a plurality of circumferentially spaced through-hole (not shown) for receives bolts to secure the probe 10 to a wall of the duct 12. An electronic enclosure 20 is disposed at one end of the probe 10 to house the electronics and pneumatic interface to each of the sensor pods 14. The lance 16 is formed of a plurality of sensor pods 14 interconnected by a plurality of pipes, tubes or conduits 22 with an end cap 24 to close off the open end of the lance. In the embodiment shown in FIGS. 1 and 2, the multi-sensor probe 10 includes three (3) sensor pods 14 disposed along the length of the lance 16. In one embodiment the outer diameter of the lance is approximately 3 inches with a length of about 30 feet. One will appreciate that the length of the lance 16 may be of any length needed to extend into and across the duct 12. The multi-sensor probe 10 may include 1 to as many as 20 sensor pods 14. The limiting factor in the number of sensor pods 14 on a sensor probe 10 is the diameter of the lance 16, which need to be great enough to accommodate all the tubes and electrical cables of each sensor pod 14 passing through the lance 16.

A shown in FIGS. 1 and 2, the multi-sensor probe 10 may be secured to a side wall of the duct 12 at only one end. One will appreciate that the multi-sensor probe 10 may be secured to a top, side or bottom wall of the duct 12. For multi-sensor probes 10 which may be too long to be supported at one end, the lance 16 of the probe 10 may be further supported within a tubular casing (not shown) that is permanently secured between the side walls of the duct 12. The casing would have openings disposed along its length corresponding to the sensors 90, 100 of the sensor pods 14. Alternatively, the lance 16 of the multi-sensor probe 10 may be a rounded tray or bridge having its ends secured between the side walls of the duct 12.

Referring to FIGS. 3-6, each sensor pod 14 includes a pair of ports or openings 30, 32 to receive gas flowing through the duct 12. An oxygen sensor 100 is disposed in one port 30 and a temperature sensor 90 disposed in the second port 32 measure respectively the oxygen and temperature of the gas flowing through the duct 12. As shown in FIG. 1, the openings of the pods open downstream of the direction of the gas flow 40 to reduce or prevent any particles or material entrained in the gas from entering or eroding the ports 30, 32.

As best shown in FIGS. 3-6, the sensor pod 14 includes a generally cylindrical body 42 which may have a planar recess 44 in the outer surface 46 of a front side or downstream side of the body. The first port 30 and second port 32 are disposed in the planar surface of the body 44 to provide passage from the gas in duct 12 to the oxygen and temperature sensors 100, 90 respectively disposed therein. An access opening 50 is also provided to enable internal access to assemble and/or repair the sensor pod 14. A cover 52 is attached to close the access opening 50, which is secure to the sensor body 42 by at least one fastener 54, such as screws, bolts or other means to secure the cover to the sensor body. The outer surface 46 of the cover 52 is contoured to match the outer contour of the sensor body 42. The inner surface (not shown) of the cover 52 includes a protrusion which matches the shape of the access opening 50 to properly locate and position the cover 52 within the access opening. A seal or gasket (not shown) may be disposed between the cover 52 and sensor body 42 to provide an air tight seal therebetween.

Figure 5:
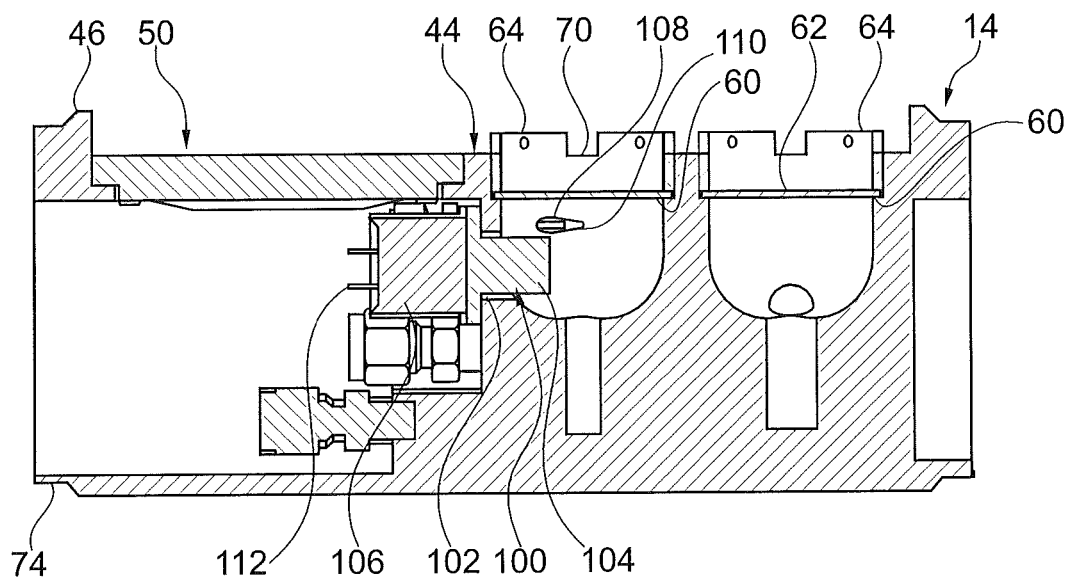
FIG. 5 is a cross-sectional view of the body of the sensor pod of FIG. 4 taken along the line 5-5.

As best shown in FIGS. 3 and 5, the first and second ports 30, 32 of each sensor pod 14 are generally cylindrical or cup shaped, wherein the outer portion of the port has a greater diameter to provide an annular lip 60 for supporting a screen or mesh 62 at the mouth of the ports 30, 32. The screen 62 may be formed of a material that can withstand a temperature range of greater than 1000° F., which may include stainless steel or other metallic material. The openings of the screen 62 are such to permit free flow of gas through the screen but sufficiently small to filter expected particles entrained in the gas flow. For a boiler application, the openings in the screen 62 may be sized to prevent particles in the range of 0.5 to 5 microns from passing. The outer portion of the first and second ports 30, 32 is also threaded to receive a pair of threaded locking rings 64 to removable secure the respective screens 62 within the ports 30, 32. When fully installed the rings 64 may extend above the planar surface 66 of the cylindrical body 42 to a height approximately at the outer surface 46 of the cylindrical body 42. The end portion 68 of the rings 64 ending above the planar surface 66 have a plurality of notches 70 dispose circumferentially-spaced around the rings, which extend downward to approximately the planar surface. The notches 70 provide a means to rotate and secure the rings. The end portions of the rings 70 also include a plurality of through holes 72 to allow a tether (not shown) between the two rings to prevent rotation after the locking rings 64 are fully inserted and the screen 62 fully captured. The ends 74 of the cylindrical body 42 are recessed or tapered circumferentially to receive and secure, such as by welding, one of an interconnecting pipes, tubes or conduits 22 or end cap 24 as discussed hereinbefore with reference to FIGS. 1 & 2. The ends 72 of the cylindrical body 42 may also be threaded for attachment to the interconnecting pipes 22 or end cap 24.

Figure 4:
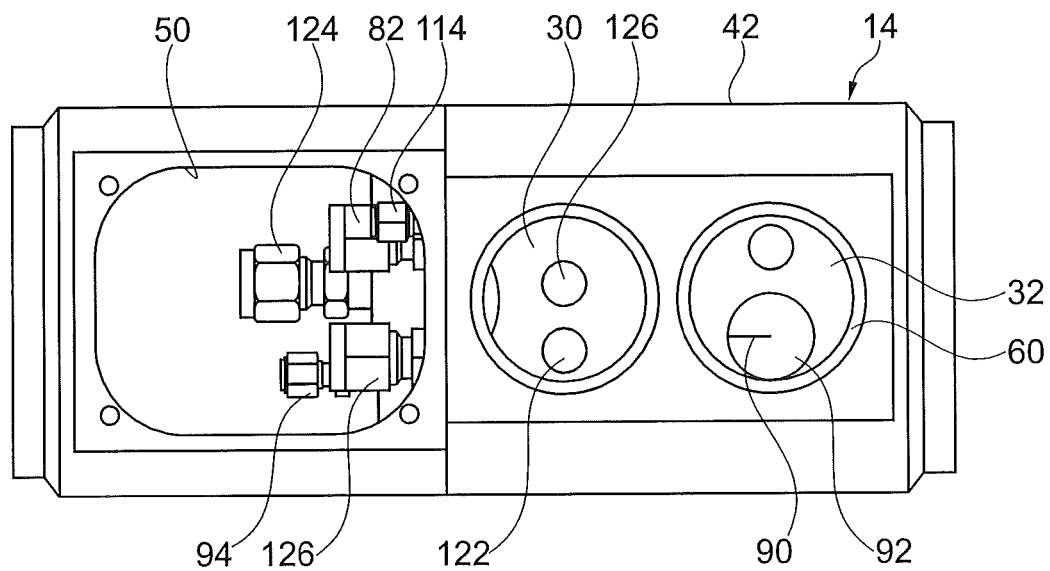
FIG. 4 is a front plan view of the body of the sensor pod of FIG. 3.
Figure 7:
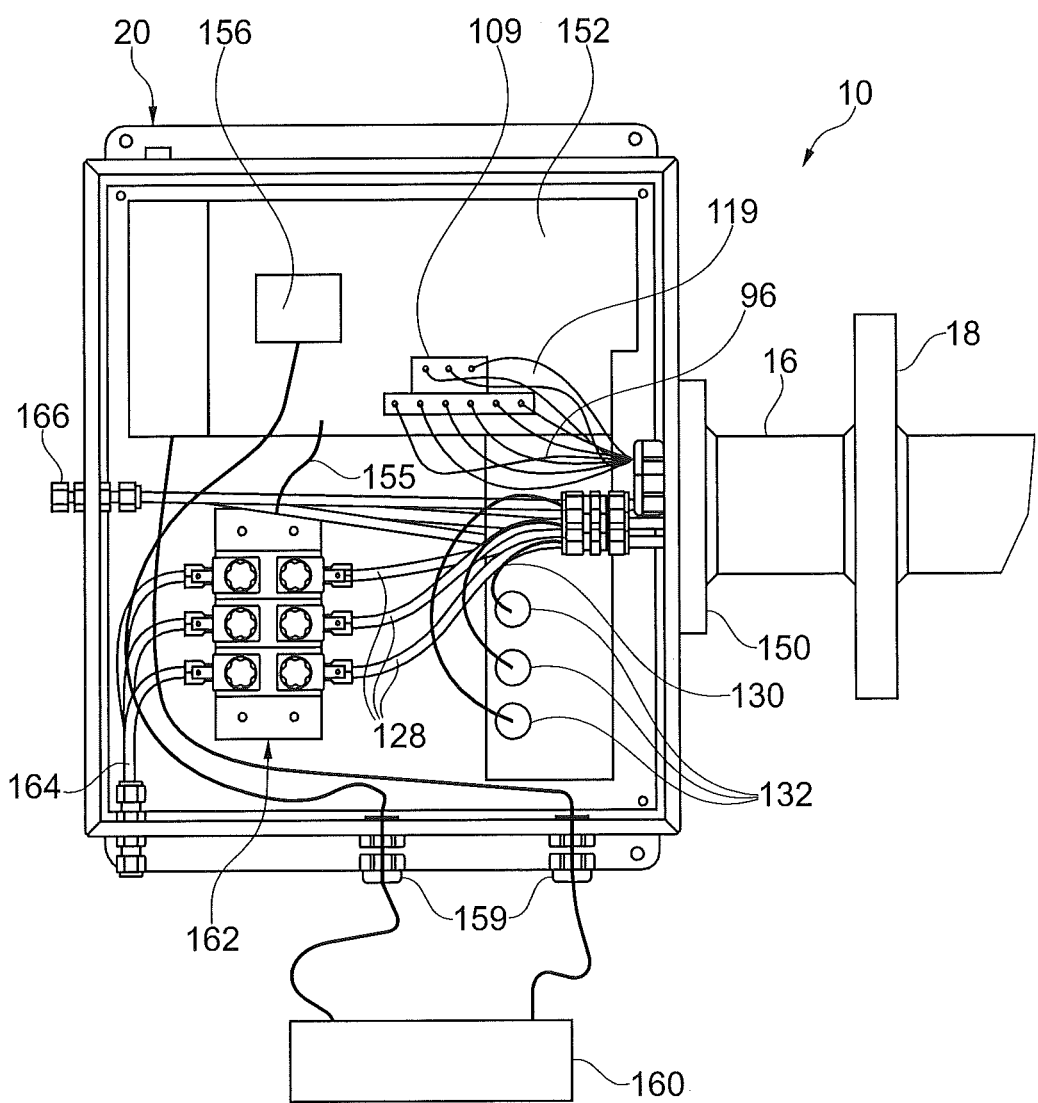
FIG. 7 is front plan view of an electronic and control valve assembly of the gas sensor of FIG. 1.

Referring to FIGS. 4 and 5, the second port 32 includes a gas extraction passageway or conduit 80 that extends from a lower portion of the second port 32 to a fitting 82. The gas extraction passageway 80 provides a means for drawing or extracting a gas from the duct 12. As shown in FIG. 7, a tube 84 extends from the electronic enclosure through the lance 16 to the gas extraction passageway. The tube 84 is attached to the gas extraction passageway 80 by the fitting 82 to permit easy attachment and removal of the tube to the extraction passageway 80. One will appreciate that any removable or permanent attachment means to fluidly connect the tube 84 to the extraction passageway, such as welding or adhesive, may be used. This ability to extract gas from the multi-sensor probe 10 at each measurement location and transporting it outside the probe enables additional measurements of the gas flowing through the duct 12. These measurements may be for properties of the gas for which no sensor technology is available that cannot operate reliably in the conditions found inside the multi-sensor probe 10, for example, Carbon Monoxide (CO), Hydrogen Sulfide (HS), Dioxen, Furans, and other, corrosive or reactive chemicals or to meet, requirements to supply continuous stream of gas from gas duct 12, to sensors not capable of continuous operation, or limited physical space.

A temperature sensor 90 also extends through a passageway or conduit 92 that extends from a fitting 94 to the inner portion of the second port 32 to measure the temperature of the gas within the duct 12. The temperature sensor 90 may include a or other types of thermal sensors known in the art. The wiring or cable 96, as shown in FIG. 7, to the temperature sensor 90, which extends from the electronic enclosure 20 and through the lance 16 and is secured to the cylindrical body 42 with a gas tight seal by the fitting 94.

Figure 6:
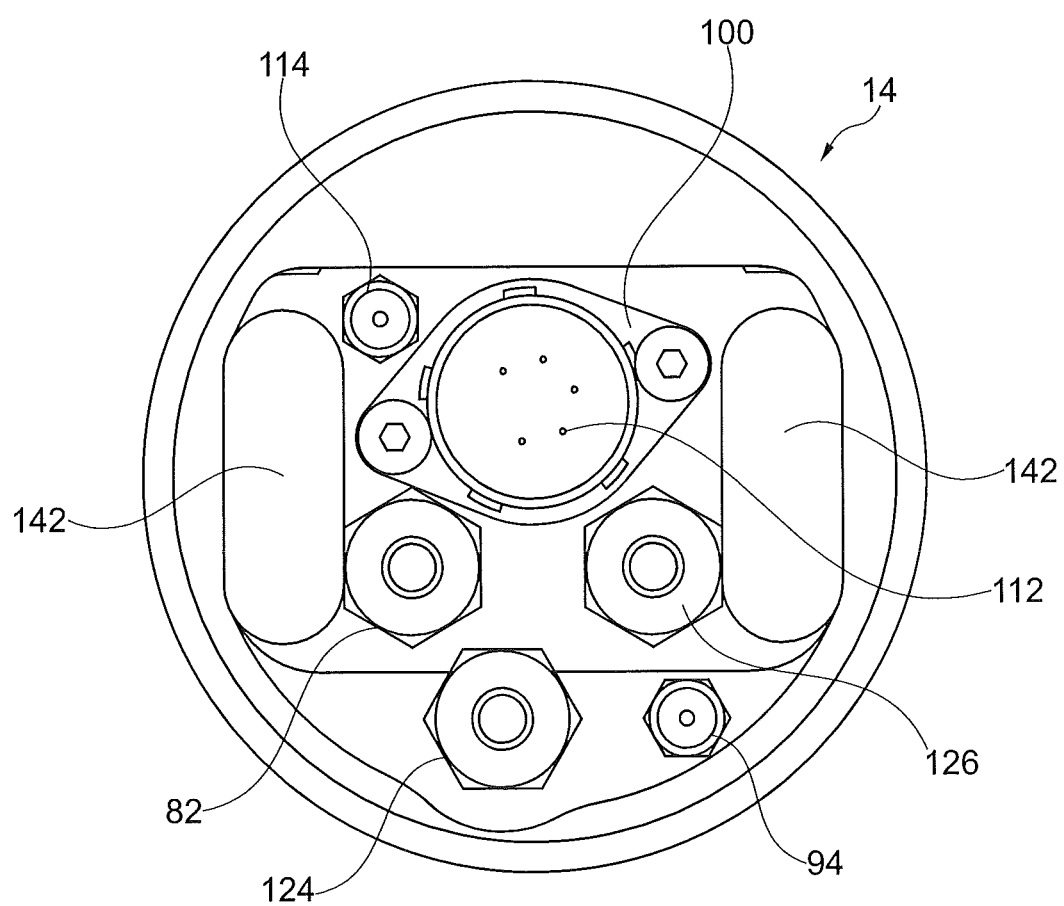
FIG. 6 is an end plan view of the body of the sensor pod of FIG. 4.

The first port 30 receives an oxygen sensor assembly 100 through an opening 102 in a side wall of the first port. The oxygen sensor assembly 100 may include a zirconium oxide sensor having a measurement portion 104 that extends into the first port 30 to measure the oxygen content of the gas within the duct 12 and a connector portion 106 mounted to an outer wall of the second port as best shown in FIG. 6. The oxygen sensor may include a dual junction zirconium oxide sensor, which does not require a constant fixed reference gas to be supplied to one side of the zirconium oxide sensor as described in US Patent Application Pub. No. 2014/0360249, but uses a pumping action to extract oxygen molecules from the surrounding gas. The zirconium oxide oxygen assembly 100 contains high temperature wiring and insulation to withstand the elevated temperatures in a boiler gas duct 12. The dual junction zirconium oxide oxygen sensor is best provided with 5 electrical connections. Two connections are for an internal heater to raise the sensing element temperature to the desired value and two connections are for the measurement voltage signal and one connection to pump. The oxygen sensor assembly 100 electrical cable extends from the electronic enclosure 20 through the lance 16 and is secured to the leads 112 of the oxygen sensor by a weld connection. This welded joint is protected by an insulated potting material for mechanical protection (not shown). One will appreciate that the zirconium oxide oxygen sensor assembly 100 may be substituted with a tin oxide sensor for measuring the carbon monoxide (CO) concentration of the gas in the first port 30. Alternately, a second sensor for measuring a gas concentration such as carbon monoxide may be added to the first port 30, or to an additional port added to each sensor pod.

A temperature sensor 108 may also extend into the first port 30 or in fluid communication with the gas within the first port 30 via a passageway or duct 110 to measure the temperature near the oxygen sensor or measure the temperature of the oxygen sensor itself. This measurement provides information on the temperature of the oxygen sensor assembly 100. Knowledge of this temperature can be useful for controlling the current to the oxygen sensor assembly 100 internal heater or providing temperature correction for the output of the oxygen sensor assembly 100. The temperature sensor 108 may include a thermocouple or other types of thermal sensors known in the art. The respective wiring or cable 116 to the temperature sensor 108 extends from the electronic enclosure 20 through the lance 16 and is secured to the cylindrical body 42 by gas tight fitting, 114.

One will appreciate that the precise temperature of the oxygen sensor assembly 100 is not required provided the sensor is operating within the normal operating range of the duct (i.e., 500 to 800 deg F.). Should extreme temperatures above the typical temperatures be reached, it is recommended to reduce the current heating the oxygen sensor assembly 100 to reduce the likelihood that the sensor is damaged.

Referring to FIGS. 4, 5 and 7, the first port 30 further includes a first passageway or conduit 120 designed to provide purge and calibration gas and a second passageway or conduit 122 designed to provide indication of pressure within the port within the body 42 of the sensor pod 14. The first and second passage ways 120, 122 provide respective fluid flow between the first port 30 to tubes 128, 130 respectively. The tubes 128, 130 are attached to the passageways by a gas-tight fittings 124, 126 respectively, to permit easy attachment and removal of the tubes to the respective passageways. One will appreciate that any removal or permanent attachment means, such as welding or adhesive may be used. The tubes or conduits 128, 130 extend from the electronic enclosure 20 through the lance 16 to the respective fitting 124, 126 secured to the cylindrical body 42 of the sensor pod 14.

As will be described in greater detail hereinafter, the first tube 128 provides air or a known concentration of oxygen from the electronic enclosure 20 to the first port 30. Air is selectively provided to the first port 30 via the first passageway 120 to force air outward through the screen 60 to clear any particles off the screen that may be clogging the openings in the screen. In addition, oxygen of a known concentration is provided to the first port 30 via the first passageway 120 to calibrate the oxygen sensor assembly 100. As will be described in further detail hereinafter, the electronic enclosure 20 may provide a plurality of different levels of oxygen concentration to the first port 30 to calibrate the oxygen sensor assembly 100 at different oxygen levels or limits, such as at an upper and lower operating range of the oxygen sensor assembly 100.

The second tube 130 and second passageway 122 provides a means for measuring the pressure within the first port 30, which is used to calibrate and compensate the oxygen sensor assembly 100. Specifically, the second tube 130 and the second passageway 122 provide fluid communication between a differential pressure sensor 132 disposed in the electronic enclosure 20 as shown in FIG. 7 and the first port 30.

As shown in FIGS. 4-6, the ends 140 of the probe body 42 are generally tubular with a pair of through channels 142 disposed therebetween to accommodate the oxygen sensor assembly cable, temperature sensors cables 96, 109, and associated tubing 84, 128, 130 disposed therein and passing therethrough. FIG. 6 provides an end view of the partially assembled sensor pod 14 of FIG. 5 which shows the laterally opposing through channels 142 to accommodate the tubing 84, 128, 130 and cables 96, 109 and oxygen sensor assembly cable from sensor pods 14 disposed further down the length of the lance 16 of the multi-sensor probe 10.

As shown in FIG. 7, the electronic enclosure 20 is attached to a flange 150 disposed at one end of the lance 16. The electronic enclosure receives the tubes 84, 128, 130 and electrical cables 96, 109 and oxygen sensor assembly cable from each sensor pod 14 disposed along the lance 16. A circuit board 152 is disposed in the electronic enclosure 20 for receiving the electronic signals from the oxygen sensor assemblies 100 and temperature sensors 90, 108. The circuit board 152 further includes a plurality of differential pressure sensors 132 in fluid communication with a respective tube 130 in fluid communication with a first port 30 of a respective sensor pod 14. Each of the pressure sensors 132 provides an electrical signal indicative of the pressure within the corresponding first port 30. The pressure 132 measure the differential pressure between each sensor location and the atmosphere, located remotely from each measurement location on the multi-sensor probe 10. An additional barometric pressure sensor disposed on the circuit board is then combined with the differential pressure sensors to calculate the absolute pressure at the sensor location. Based on these measured signals, at least one computer processor 156 on the circuit board provides, via an external connector 158 to a user or plant digital control system (DCS) 160, an output signal or signals indicative of an oxygen content or concentration of the gas in first port 30 and/or the temperature and pressure of the gas passing through the duct 12. The circuit board also provides output signals for the remaining sensors in other pods, and status information about the probe operation, via the same external connector 158.

As shown in FIG. 7 and described hereinbefore, the tubes 128 of each sensor pod 14 provides a selected gas to the first port 30 having the oxygen sensor 100 disposed therein. A pneumatic manifold or header 162 disposed in the electronic enclosure 20 selectively provides a gas stream to a select tube 128. The pneumatic manifold 162 includes one or more gas sources controlled by a valve or solenoid which connect each of these gas sources to a common mixing location. One or more connections also controlled by a valve or solenoid are provided to direct the selected gas to each of the outlets. In the embodiment shown in FIG. 7, three (3) different gasses are provided to the input of the pneumatic manifold 162 via input tubes or conduits 164 fluidly connected to respective inputs of the pneumatic manifold. A first of the input tubes 164 has air or other appropriate gas for cleaning or unclogging the screens 62 disposed in the first port 30 of the sensor pod 14. A second one of the tubes has a gas with a known concentration of oxygen approximately at or just above the lower measurement limit of the desired operating/measurement range of the oxygen sensor assembly 100. A third one of the tubes has a gas with a known concentration of oxygen approximately at or just below the upper measurement limit of the desired operating/measurement range of the oxygen sensor 100. For instance, for an oxygen operating range of 0-10% oxygen concentration, the calibration gas having the lower oxygen concentration may have a concentration between 0 and 0.4% and the higher oxygen concentration may have a concentration between 8 and 10%. The tubes 128 of each sensor pod 14 is fluidly connected to respective outputs of the pneumatic manifold 162 to selectively receive one of the three input gas streams provided to the inputs of the pneumatic manifold. In response to a control signal via 155 from the processor 156 of the circuit board 152, the pneumatic manifold 162 selectively provides one of the three input gases to one or described above, the gas streams are used during the oxygen calibration process and the screen cleaning process. The processor 156 also controls the timing and duration of the selected gas provided to the first port 30 of the sensor pods 14.

As shown in FIG. 7 and describe hereinbefore, the tubes 84 providing the extraction gas from the second port 32 is provided to respective external connectors 166 to permit connection of the tubes to various other sensors or sensing apparatus that may measure other constituents of the gas, such as NOx, CO, $CO_2$, SOx, and nitrogen, for example.

The processor 156 disposed in the electronic enclosure 20 may perform a calibration of the oxygen sensor 100 of each sensor pod 14 periodically, in response to an external input signal from the DCS 160, or in response to an operating condition of the oxygen sensor determined by the processor. During the calibration process, a selected oxygen sensor 100 is calibrated at an oxygen level at both the low end and the high end of the expected operating range of the oxygen sensor. One will appreciate that the operating range differs depending on the expected oxygen range and the location of the sensor probes in the system. For example, the oxygen level or concentration at the low end of the operating range may be approximately 0.4% and approximately 10% at the high end of the operating range. In response to a command for initiating the calibration process, the processor 156 provides a signal to the pneumatic manifold 162 to fluidly provide one of the known oxygen input streams to the tube 120 of the selected first port 30 of the oxygen sensor 100 to be calibrated. The known oxygen input stream may be the stream corresponding to the known low concentration level or the known high concentration level. Once the low concentration level is selected and sufficient time passes to allow the selected first port 30 to fill with the known oxygen stream, the processor 156 then measures the oxygen level, temperature and pressure within the first port of the selected sensor pod 14. The processor 156 then determines or calculates the expected measured oxygen level, compensated for temperature and pressure, in the first port 30. The expected measured low oxygen level is then compared to the measured low oxygen level, compensated for temperature and pressure, to define the difference between these two values. Once this low level difference is determined, the same steps are followed to provide and measure the known high level stream to the first port 30 having the oxygen sensor 100 under calibration. The expected measured high oxygen level is then compared to the measured high oxygen level to define the difference between these two values. The value of measured difference at the low level and the value of the measured difference at the high level are used to define, calculate or determine a calibration curve or factor to compensate the measurement of the oxygen sensor 100 over the expected operating range. The calibration curve may be linear or non-linear. The oxygen sensors 100 may be calibrated separately from the other oxygen sensors disposed along the lance 16. Consequently, this permits the other oxygen sensors 100 on the multi-sensor probe 10 to continue measuring the gas within the duct 12 while the selected oxygen sensor is undergoing calibration. The present invention further contemplates that only a single calibration gas having a known oxygen concentration is used to calibration the oxygen sensor 100. In the instance, the single calibration gas has a concentration approximately at or just below the upper operating concentration of the system to calibrate the upper limit of the oxygen sensor 100. The lower end of the calibration is assumed to be 0% concentration. Using only one calibration gas may be less accurate, but requires less hardware and gas to calibration the oxygen sensor 100.

Figure 8:
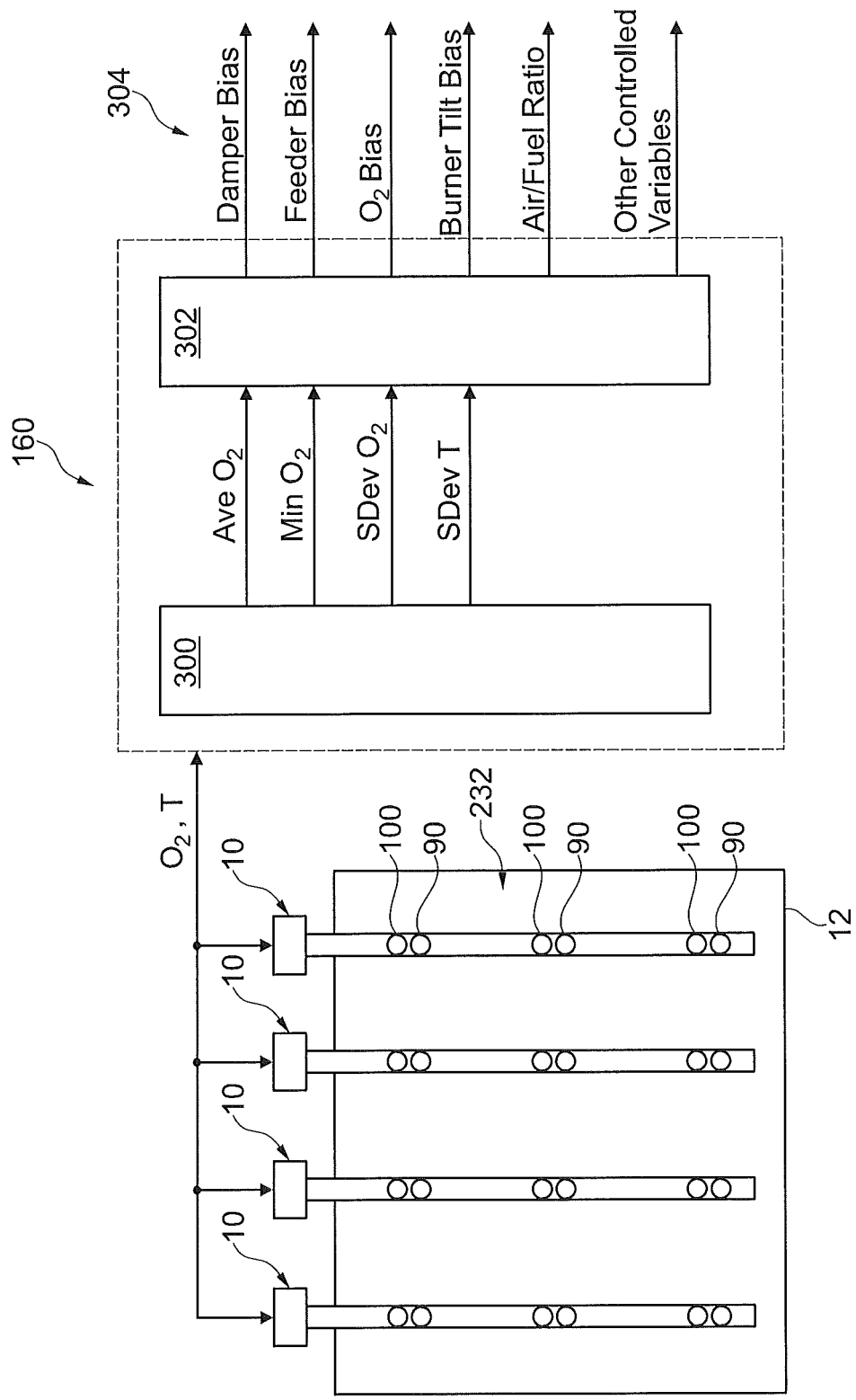
FIG. 8 is a cross-sectional view of a duct of the combustion power plant showing a plurality of gas probes disposed therein according to the present invention.

Referring to FIG. 8, a plurality of multi-sensor probes 10 of FIGS. 1-7, is shown disposed within a duct 12 for measuring at least the temperature and oxygen across a cross-sectional area of the duct. As shown, four (4) multi-sensor probes 10 are spaced from each other, wherein each probe includes three (3) sensor pods 14 to measure temperature and oxygen within the duct 12. The multi-sensor probes 10 provide a grid or array of oxygen and temperature sensors 90, 100 across the duct 12 to provide a thermal and oxygen profile of the gas flowing therethrough. Each of the multi-sensor probes 10 provide the oxygen and temperature measurements to a computer, controller, processor or DCS 160 which may use this information to control the operation of associated equipment, to identify needed maintenance of associated equipment, to determine the condition or efficiency of the associated equipment, and/or to identify the need to calibrate or replace any of the oxygen sensors 100.

Figure 9:
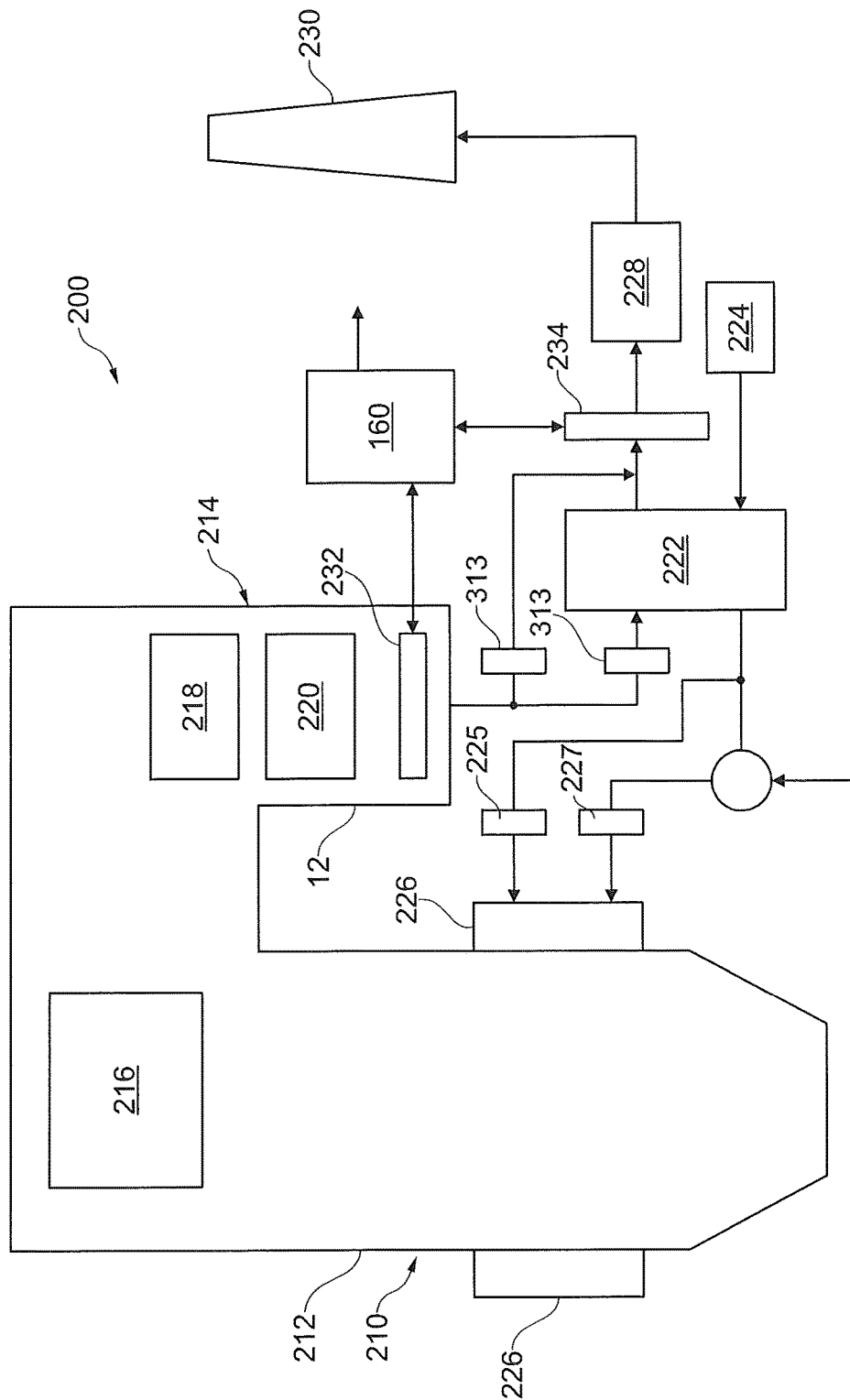
FIG. 9 is a block diagram a combustion power plant having a gas outlet monitoring system according to claim 1.

For example, the plurality of multi-sensor probes 10 may be disposed within a duct 20 of a power plant 200, such as a coal-fired boiler plant, as shown in FIG. 9 to improve the operation of the power plant, more accurately measure the operation of components of the power plant, and identify malfunctions in the power plant. For instance, the array of sensors 90, 100 can provide measurements to control the boiler fuel to air ratio for optimum emissions control and heat rate, which also allows more accurate control and minimizes potential for high carbon monoxide (CO) and associated hazardous air pollutant (HAP) emissions and possible boiler corrosion. The control of the fuel to air ratio may also be controlled to minimize dry gas heat loss and maximize combustion efficiency and overall boiler efficiency. The array of oxygen and temperature sensors 90, 100 may also identify and minimize imbalances in oxygen and temperature in the duct 12, and consequently, the power plant 200. Air leakage in an air heater 222 and the dew point of the air heater may be measured and monitored online to determine the optimum heat rate and maintenance planning of the air heater 222. The plurality of multi-sensor probes 10 may also identify a malfunction in the combustion system.

In FIG. 9, an exemplary coal-fired plant 200 includes a boiler 210 where the combustion of fuel 211, such as coal, takes place to heat feed water passing through waterwalls 212 to generate steam to drive a turbine (not shown) to produce electricity. The combustion of the fuel 211 creates flue gas which may contain $CO_2$, NOx, CO, SOx, $O_2$ and other hazardous air pollutant (HAP), such as mercury, arsenic, heavy metals, as well as dioxins and furans. The flue gas passes through a duct or back pass 214 wherein a plurality of heat exchangers 216, 218, such as superheaters, which further heat the feedwater or steam flowing through the water wall tubes, and an economizer 220 for cooling the flue gas before exiting the back pass duct 12. The flue gas then passes through an air heater 222 to heat a countercurrent air stream 224 flowing therethrough. The heated air 224 flows to a plurality of burners or air nozzles (not shown) located in a windbox 226. The amount of heated air and fuel provided to the boiler or combustion chamber 210 is regulated by respective dampers and fans 225, 227. The fuel 211 is provided to the burner with the heated air exiting the air heater 222 for combustion in the boiler 210. The flue gas exiting the air heater flows through a duct to at least one air quality control system (AQCS) 228, such as a particle filter, selective catalyst reduction system (SCR) and/or a wet or dry flue gas desulfurization (FGD) system. The flue gas from the AQCS 228 is release to the atmosphere via a stack 230.

Referring to FIG. 9, a first set of multi-sensor probes 232, as shown in FIG. 8, is disposed in the duct downstream of the economizer 220 and upstream of the air heater 222 of the boiler plant 200 for controlling the operation of the boiler plant. The first set of multi-sensor probes 232 provides at least oxygen and temperature measurements over the cross-section area of the backpass duct 12 to the DCS 160. The first set of multi-sensor probes 232 may also measure other constituents of the flue gas extracted from the duct 12 via the second port 32 to control the operation of the boiler 210.

Referring to FIG. 8, the computer, controller, processor or DCS 160 includes a calculation module 300 that calculates or determines the average oxygen concentration ("Ave $O_2$") in the duct 12 by averaging the results of each oxygen sensor 100 on each multi-sensor probe 10 disposed in the duct 12. The calculation module further determines the lowest oxygen concentration ("Min $O_2$") measured by the oxygen sensors 100. The calculation module 300 also determines the standard deviation of the oxygen concentration ("SDev $O_2$") and temperature ("SDev T") of the plurality of oxygen temperature to a model predictive controller (MPC) and/or neural network, to provide control signals (CVs) 304 for operating the various components or systems of the power plant. In response to received input variables (IVs), the controller 302 provides one or more control variables (CVs) which control various components and/or systems for operating the power plant. The input variables include the plurality of oxygen and temperature measurements from the array of sensor pods 14 from the calculation module 300, as well as the plant information on air and fuel flows as represented by DCS tags. The control variables include at least the "Damper Bias" for controlling the position of a damper or valve or speed of a fan 225 which controls the amount or rate of primary and/or second air 224 provided to the combustion chamber or nozzles in the windbox 226, the "Feeder Bias" for controlling the position of a damper or valve 227 to control the amount or rate of fuel 211 provided to the combustion chamber or nozzles, the "$O_2$ Bias" for controlling the position of a damper or valve to control the amount or rate of oxygen provided to the combustion chamber or nozzles, and for controlling an actuator to adjust the degree of tilt of one or more selected nozzles. Other control variables may include the position of dampers, speed of fans and settings of a classifier associated with a fuel pulverizer (not shown), such as a coal grinding mill. The boiler 200 may be a tangentially-fired boiler, a wall fired boiler or other boilers, such as a down-shot boiler.

Figure 10:
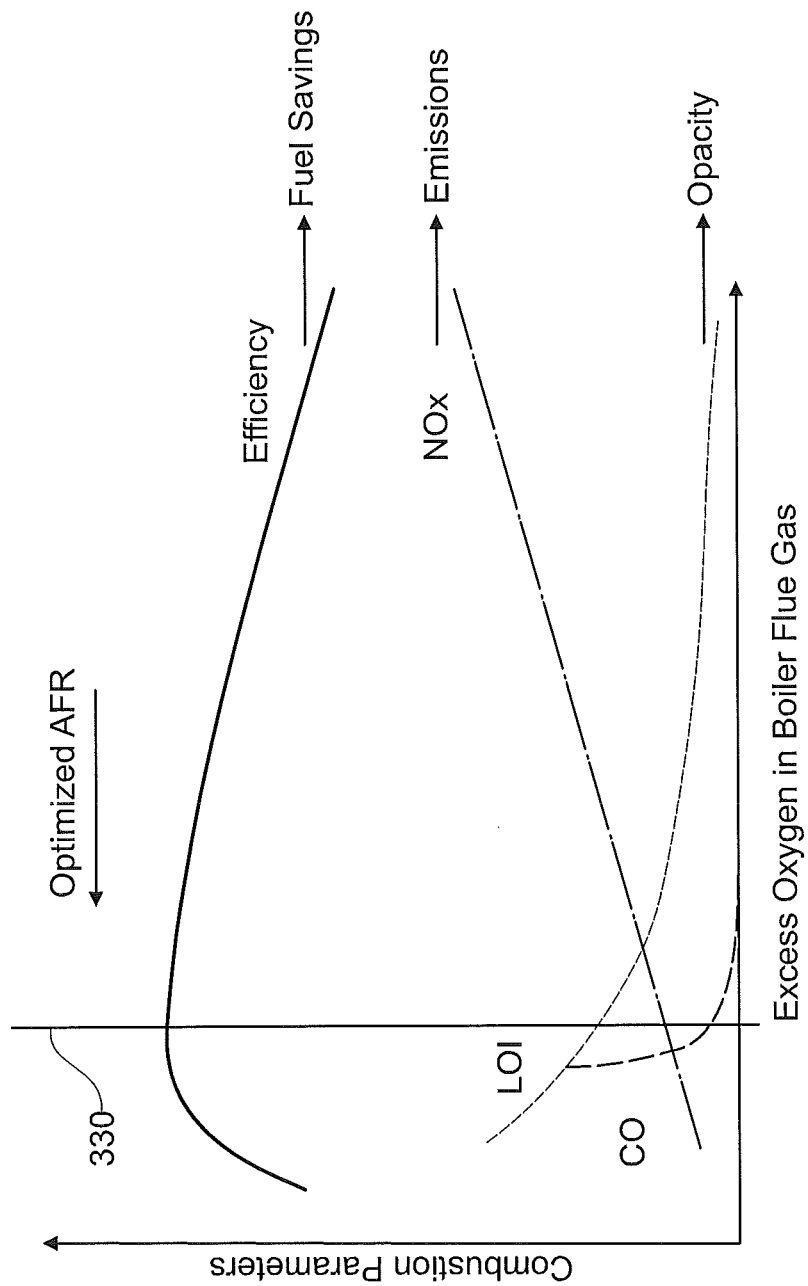
FIG. 10 is a plot of the combustion parameters of a combustion power plant versus the excess oxygen in the boiler flue gas of the combustion power plant.

The measured oxygen concentration and temperature in the backpass duct 12 downstream the economizer 220 indicates the amount of excess oxygen in the boiler flue gas or imbalance in the combustion of the boiler plant 200. The plot of FIG. 10 shows the relation of the efficiency of the boiler, the amount of emissions (i.e., NOx and CO), and the loss on ignition (i.e., the percentage of unburnt fuel passing through the backpass 214) in relation to the combustion parameters versus the amount of excess oxygen in the boiler flue gas in the backpass. As shown in the plot of FIG. 10, the amount of excess oxygen in the boiler flue gas correlates to the amount of emissions, i.e., NOx and CO, passing through the backpass. As the amount of oxygen increases, the CO level, LOI and boiler efficiency decreases, while the NOx level increases. The optimum excess oxygen level in the boiler flue gas, as shown by line 330 in FIG. 10, is determined by the maximum CO and NOx limits for the operation of the boiler 210. One will appreciate that an accurate measurement of the excess oxygen in the flue gas is needed to maintain the boiler operating at the optimum point. An oxygen measurement having an excess error may cause the operation of the boiler to produce either high levels of CO or NOx that exceed permissible limits. The level of oxygen in the boiler flue gas correlates to the combustion properties of the boiler such as the air to fuel ratio and the amount of oxygen in the combustion chamber/boiler 210. The angle or tilt of the nozzles also affects the combustion of the fuel, and thus the amount of excess oxygen in the flue gas. Consequently, as shown in FIG. 8, the controller 302 controls at least one of the amount of fuel, air, air to fuel ratio and oxygen to the combustion chamber, as well as the tilt of the nozzles, in response to the oxygen and temperature of the flue gas as measured by the array of oxygen and temperature sensors 232 in FIGS. 8 and 9. As one will appreciate, adjustment of the burner tilt also controls the steam temperatures within the waterwalls and superheaters. Consequently, the tilting of the burners may also take into account steam temperatures of the boiler 200.

Referring to FIG. 9, a second set of multi-sensor probes 234, as shown in FIG. 8, is disposed in the duct downstream of the air heater 222 and upstream of the AQCS 228 to thereby provide an array of oxygen and temperature sensors 232, 234 disposed upstream and downstream of the air heater 222 of the boiler plant 200 for controlling and/or monitoring the operation and health of the boiler plant 200 and air heater 222. This configuration is particularly useful to evaluate the condition and efficiency of the air heater 222.

Figure 12:
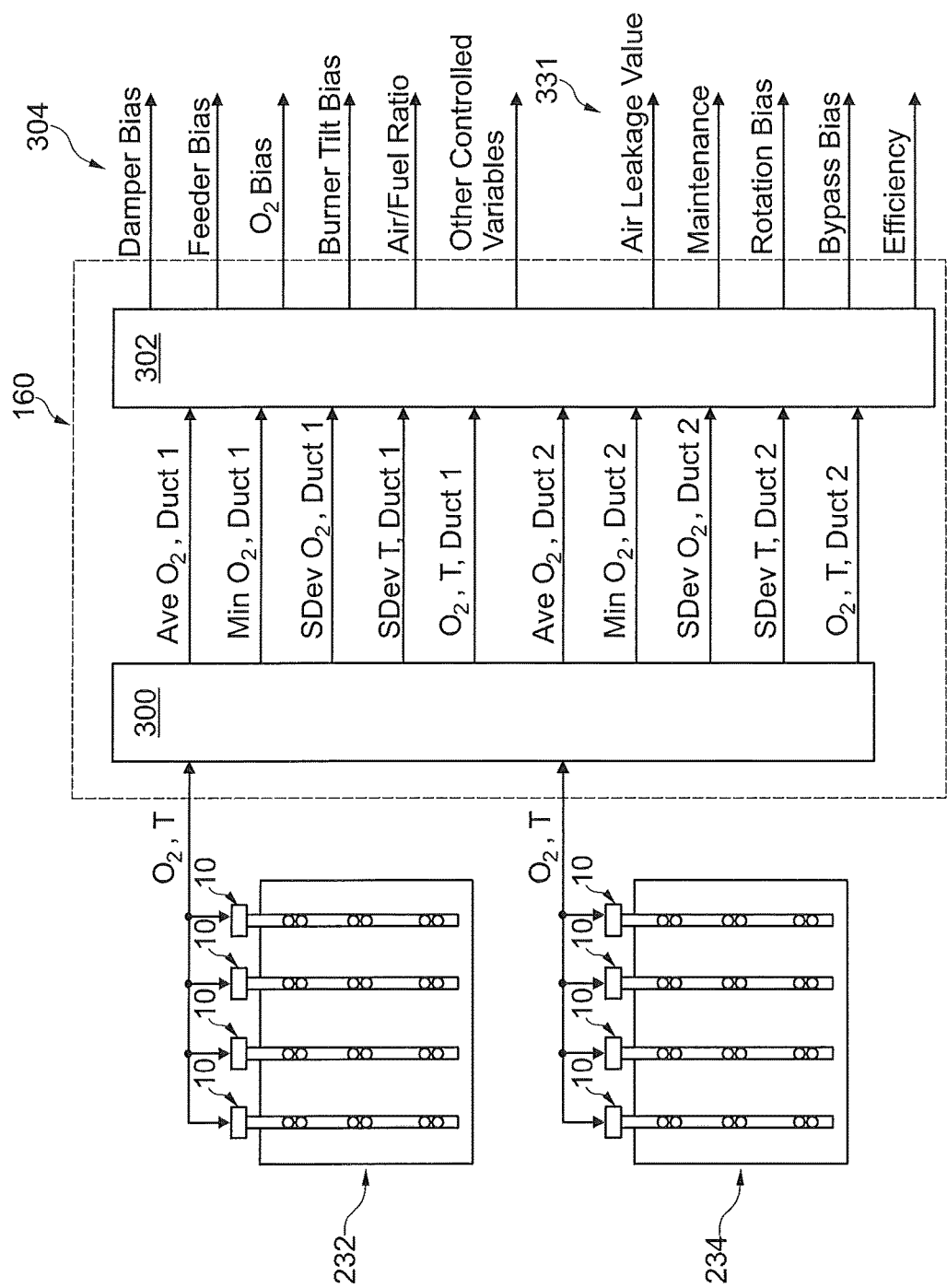
FIG. 12 is a schematic diagram of a control system for controlling the fluid flow passing through an air heater of the combustion power plant according to the present invention.

As best shown in FIG. 12, the second set of multi-sensor probes 234 provides at least oxygen and temperature measurements over the cross-section area of the duct downstream of the air heater 222 to the DCS 160. The second set of multi-sensor probes 234 may also measure other constituents of the flue gas extracted from the duct downstream of the air heater 222 via the second port 32 to monitor other parameters of the air heater 222. Furthermore, the temperature measurements after the air heater 22 can also be used to maintain flue gas temperatures safely above the acid dew point to reduce corrosion. Cold air leaking into the air heater 222 will reduce the flue gas temperature and even localized cold spots could encourage corrosion.

A shown in FIG. 12, the measurement signals from the second set of multi-sensor probes 10 are provided to the DCS 160. Similar to that shown and described in FIG. 8, the calculation module 300 calculates or determines the average oxygen concentration ("Ave $O_2$"), the lowest oxygen concentration ("Min $O_2$") measured by the oxygen sensors 100 the standard deviation of the oxygen concentration ("SDev $O_2$") and the temperature ("SDev T") of the plurality of oxygen temperature measurements measured in the respective ducts upstream and downstream of the air heater 222. In addition control signals (CVs) 304 provided in FIG. 8, the controller 302 provides additional control signals (CVs) 331 which are indicative of the operation status and efficiency of a component or system of the power plant, such as the air heater 222, as well as control signals to control the operation of the air heater. The additional input variables include the plurality of oxygen and temperature measurements from the array of sensors 90, 100 from the calculation module 300, as well as existing plant data from the DCS on air heater inlet and outlet temperatures, such as the inlet and outlet temperatures of the combustion air flowing through the air heater 222. The additional control variables further include at least an "Air Leakage Value" signal indicative of the difference of the average $O_2$ level between the input and output of the air heater on the flue gas side of the air heater, an "Efficiency" signal indicative of the performance of the air heater based on the temperature and oxygen measurements upstream and downstream of the air heater, a "Maintenance" signal based on the temperature and oxygen measurements upstream and downstream of the air heater that actuates or provides an alarm or indicator that maintenance or repair of the air heater is needed, a "Bypass Bias" signal to control one or more baffles or values 313 to adjust the amount of flue gas passing through the air heater, and a "Rotation Bias" signal to control the speed of a motor that rotates the air heater or a signal to adjust air heater seal plates.

As suggested, depending on the amount of air leakage in the air heater 222, the processor may provide a command or alarm that maintenance is necessary to repair the air heater, such as replace or adjust a seal disposed between the air side and flue gas side of the air heater. For example, the first and second set of sensor 232, 234 may determine the amount of air leakage from the input air side to the flue gas side of the air heater 222. The first set of sensors 232 upstream of the air heater 222 measures the oxygen content of the flue gas entering the air heater. The second set of sensors 234 measure the oxygen content of the flue gas exiting the air heater 222. The controller 302 of the DCS 160 compares these measured oxygen levels to determine the increase of oxygen exiting the air heater 222. This increase in oxygen concentration correlates to the amount of air leakage to the flue gas side. In the comparison of the oxygen measurements, the controller 302 may compare the average oxygen measurement of all the oxygen sensors in the upstream duct with the average oxygen measurement of all the oxygen sensors in the downstream duct. One will appreciate that the controller 302 may average any number of sensor measurements in a duct at any selected location. Further the locations of the oxygen sensors 100 in the upstream duct may different that the locations of the oxygen sensors 100 in the downstream duct.

Figure 11:
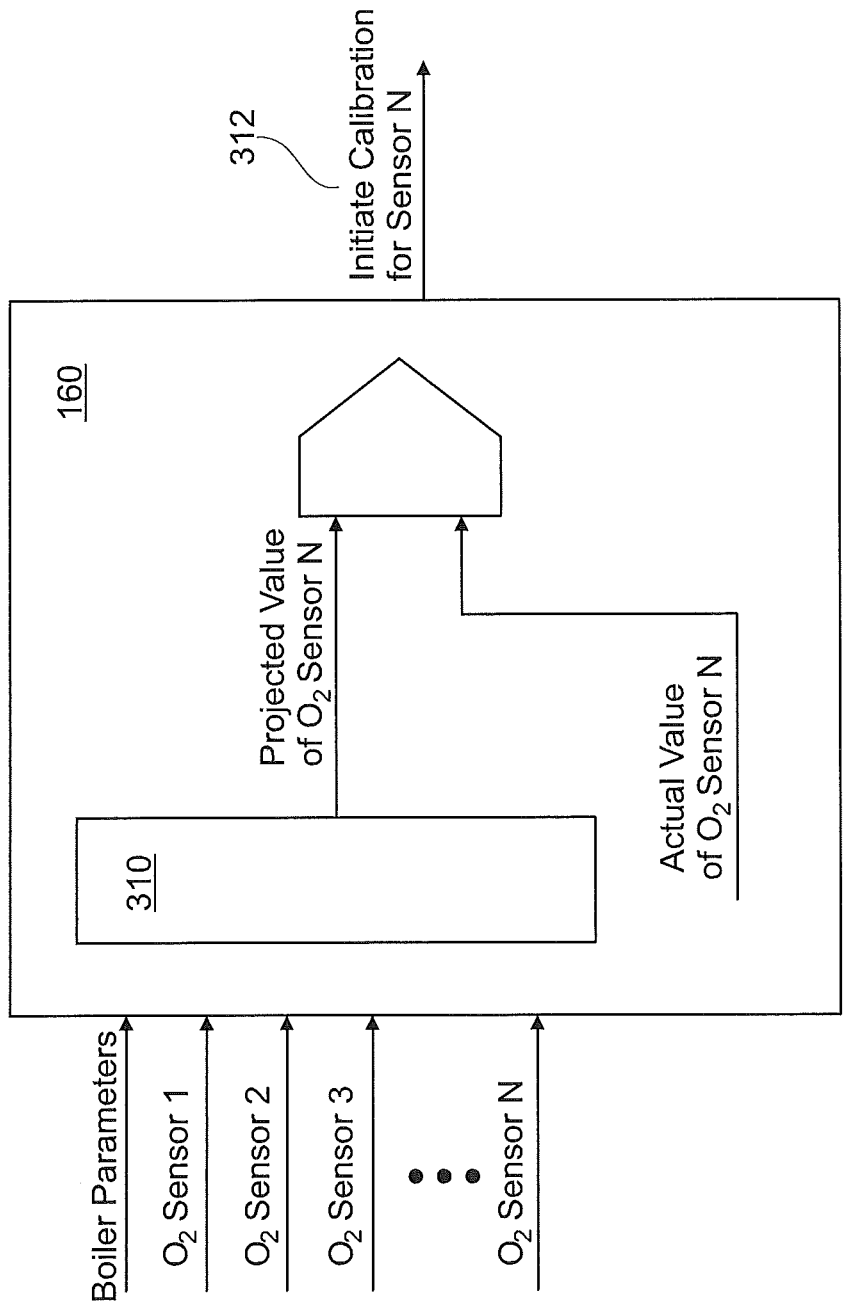
FIG. 11 is a schematic diagram of a controller for initiating calibration of a sensor of a gas sensor according to the present invention.

The DCS 160 especially if it is capable of Neural Net calculations may also monitor each of the oxygen sensors 100 of the plurality of multi-sensor probes 10 to determine the performance or accuracy of each oxygen sensor measurement being provided. As shown in FIG. 11, a controller 310 determines a projected or expected oxygen level in the flue gas duct 12 for each of the individual oxygen sensors 100 based upon one or more operating parameters of the boiler 200. These operating parameters include boiler load, air/fuel ratio, fuel flue rate, air flow rate, flue gas temperature, burner tilt, and other possible variable or adjustable operational parameters of the boiler 200. The projected value of a particular oxygen sensor 100 is compared to the actual measurement of the corresponding oxygen sensor. If the projected value and the actual value of the selected oxygen sensor 100 differ by a predetermined amount, the DCS 160 provides a calibration signal to the corresponding multi-sensor probe 10, which in response, performs the sensor calibration procedure as described hereinbefore. If the sensor cannot be calibrated, the sensor is identified as needing repair or replacement. Once the suspect oxygen sensor 100 is recalibrated revealing that the sensor is in fact operating correctly, the projected value and actual value of the measurement of the suspect oxygen sensor are again compared. If the difference is again greater than the predetermined amount, the deviation is attributable to a malfunction in the burner system. Alternatively, the suspect or faulty oxygen sensor 100 may remain in operation, wherein the DCS 160 may ignore the measurement provided by this oxygen sensor in the operation of the DCS. Alternatively, the DCS 160 may assign the projected value determined by the controller 310 and neural network in the operation of the DCS 160 and power plant 200.

Alternatively, the actual value of the measurement of each respective oxygen sensor 100 may be compared to the standard deviation value of a number of select oxygen sensors. If the actual measured value of oxygen is outside of the standard deviation of the selected oxygen sensors 100, this oxygen sensor is identified as a suspect oxygen sensor which then undergoes the calibration procedure. Alternatively, the process of calibration may be instituted on a timed basis (once per day, for example)

While this method of monitoring the performance of the oxygen sensors 100 of the multi-sensor probes 10 as shown in FIG. 11, one will appreciate that the same processor may be used to identify faulty temperature sensors 90 for replacement or repair or temporary operation of the power plant 200 until the temperature sensor is operational.

The controller 302 may evaluate the oxygen and/or thermal profile or map defined by the DCS based on the oxygen and or temperature signals of the first set of sensors 232 located in the bypass duct 12 to detect faults or problems with equipment or systems upstream of the sensors 232, For example, compared with an expected oxygen and/or thermal map predicted by the neural network, an unexpected change in oxygen concentration or temperature in the oxygen and/or thermal map, such as a drop in oxygen concentration in an area of the duct 12, may indicate a faulty or malfunctioning burner, nozzle, damper, or fan. Other potential faults may include clogs, obstructions, or air leaks in the boiler 200. These indications may initiate a shutdown of the boiler plant, maintenance or repair of specific equipment or a change in the operation of the boiler plant 200, such as changes in fuel flow, air flow, nozzle tilt and fuel grinding for example.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A multi-sensor probe comprising:
   a tubular lance;
   a plurality of sensor pods spaced along the tubular lance, each sensor pod including a first port having an oxygen sensor disposed therein, and a second port having a first temperature sensor disposed therein;
   an enclosure coupled to one end of the tubular lance, the enclosure having a plurality of pressure sensors disposed therein;
   a first plurality of tubes passing through the tubular lance, each tube of the first plurality of tubes fluidly coupled between the enclosure and the first port of a respective sensor pod of the plurality of sensor pods to selectively provide a first gas to the oxygen sensor disposed therein; and
   a second plurality of tubes passing through the tubular lance, each tube of the second plurality of tubes fluidly coupled between the first port of a respective sensor pod and a respective pressure sensor of the plurality of differential pressure sensors to provide an indication of pressure within the respective first port.

2. The multi-sensor probe of claim 1, wherein the first port of each sensor pod further having a second temperature sensor disposed therein to provide a temperature measurement of the respective oxygen sensor.

3. The multi-sensor probe of claim 1, wherein the second port of each sensor pod is fluidly coupled to a first end of a respective gas extraction tube extending through the lance, the gas extraction tube further fluidly coupled to the enclosure at a second end, to convey a second gas from the respective second port to the enclosure.

4. The multi-sensor probe of claim 1, further comprising:
   a first screen secured to an outlet of the first port; and
   a second screen secured to the outlet of the second port.

5. The multi-sensor probe of claim 1, wherein the first gas is a known gas.

6. The multi-sensor probe of claim 5, wherein the known gas is at least one of a gas having a known oxygen concentration and a purge gas.

7. The multi-sensor probe of claim 6, further comprising a processor for calibrating the oxygen sensor based upon the known concentration of the known gas provided to the first port and the pressure within the first port.

8. The multi-sensor probe of claim 6, further comprising a pneumatic manifold having a plurality of inlets and outlets and a switch to selectively provide fluid from a selected inlet to a selected outlet, wherein each tube of the first plurality of tubes are fluidly connected to respective outlets of the pneumatic manifold, wherein the known gas is provided to respective inlets of the pneumatic manifold.

9. The multi-sensor probe of claim 1, wherein the plurality of sensor pods include one of two, three, four, five and six sensor pods spaced along the lance.

10. A method for measuring constituents of a gas flowing a duct; the method comprising:
    measuring an oxygen concentration and a temperature within the duct at multiple locations within the duct using at least one multi-sensor probe extended within the duct; the multi-sensor probe including:
    a tubular lance;
    a plurality of sensor pods spaced along the lance, each sensor, pod including a first port having an oxygen sensor disposed therein, and a second port having a first temperature sensor disposed therein:
    an enclosure coupled to one end of the tubular lance, the enclosure having a plurality of pressure sensors disposed therein;
    a first plurality of tubes passing through the lance, each tube of the first plurality of tubes fluidly coupled between the enclosure and the first port of a respective sensor pod of the plurality of sensor pods to selectively provide a first gas to the oxygen sensor disposed therein; and
    a second plurality of tubes passing through the lance, each tube of the second plurality of tubes fluidly coupled between the first port of a respective sensor pod and a respective pressure sensor of the plurality of differential pressure sensors to provide an indication of pressure within the respective first port; and controlling an operational parameter of the boiler in response to the plurality of temperature and oxygen measurements provided from the multi-sensor probe.

11. The method of claim 10, wherein multi sensor probe includes a plurality of multi-sensor probes disposed within the duct.

12. A gas outlet monitoring system for controlling the operation of a boiler; the system comprising:

a plurality of multi-sensor probes disposed within a duct of the boiler; each multi-sensor probe including:

a tubular lance;

a plurality of sensor pods spaced along the lance, each sensor pod including a first port having an oxygen sensor disposed therein, and a second port having a first temperature sensor disposed therein;

an enclosure coupled to one end of the tubular lance, the enclosure having a plurality of pressure sensors disposed therein;

a first plurality of tubes passing through the lance, each tube of the first plurality of tubes fluidly coupled between the enclosure and the first port of a respective sensor pod of the plurality of sensor pods to selectively provide a first gas to the oxygen sensor disposed therein; and a second plurality of tubes passing through the lance, each tube of the second plurality of tubes fluidly coupled between the first port of a respective sensor pod and a respective pressure sensor of the plurality of differential pressure sensors to provide an indication of pressure within the respective first port;

a processor communicatively coupled to the plurality sensors pods, the processor operative to receive oxygen concentration and temperature information from the sensor pods, and to control an actuator to change an operation parameter of the boiler in response to the respective oxygen concentration and temperature information received from the sensor pods of the respective multi-sensor probes.

13. The gas outlet monitoring system of claim 12, wherein the plurality of multi-sensor probes measure flue gas passing through the duct and are downstream of an economizer of the boiler, and the processor controls the flow of at least one of the fuel and gas to the boiler.

14. The gas outlet monitoring system of claim 12, wherein the plurality of multi-sensor probes measure a flue gas passing through the duct.

15. The gas outlet monitoring system of claim 12, wherein the processor includes a neural network.

16. The gas outlet monitoring system of claim 12, wherein the plurality of multi-sensor probes comprises a first plurality of multi-sensor probes disposed upstream of an air heater; and a second plurality of sensor probes disposed downstream of the air heater.

17. The gas outlet monitoring system of claim 16, wherein the processor provides an indicator in response to the oxygen and temperature measurement provided by the multi-sensor probes upstream and downstream of the air heater.

* * * * *